(12) United States Patent
Chetoni et al.

(10) Patent No.: US 8,664,197 B2
(45) Date of Patent: Mar. 4, 2014

(54) OPHTHALMIC COMPOSITIONS CONTAINING MUCOADHESIVE POLYSACCHARIDES ABLE TO PROMOTE CORNEAL RE-EPITHELIZATION

(75) Inventors: Patrizia Chetoni, Pisa (IT); Susi Burgalassi, Pisa (IT); Daniela Monti, Pisa (IT); Marco Fabrizio Saettone, Viareggio (IT)

(73) Assignee: Opocrin S.p.A., Corlo di Formigine (MO) (IT)

( * ) Notice: Subject to any disclaimer, the term of this patent is extended or adjusted under 35 U.S.C. 154(b) by 933 days.

(21) Appl. No.: 12/063,623

(22) PCT Filed: Aug. 10, 2006

(86) PCT No.: PCT/IT2006/000616
§ 371 (c)(1),
(2), (4) Date: Mar. 8, 2010

(87) PCT Pub. No.: WO2007/020671
PCT Pub. Date: Feb. 22, 2007

(65) Prior Publication Data
US 2010/0160252 A1    Jun. 24, 2010

(30) Foreign Application Priority Data
Aug. 12, 2005   (IT) .............................. RM2005A0443

(51) Int. Cl.
*A61K 31/715*   (2006.01)
*A61P 27/04*   (2006.01)

(52) U.S. Cl.
USPC .......................................................... 514/54

(58) Field of Classification Search
USPC .......................................................... 514/54
See application file for complete search history.

(56) References Cited

U.S. PATENT DOCUMENTS

| 4,039,662 A | 8/1977 | Hecht et al. |
| 6,008,170 A * | 12/1999 | Tanaka et al. ................. 510/114 |
| 2004/0266725 A1 * | 12/2004 | Inohara et al. .................. 514/54 |

FOREIGN PATENT DOCUMENTS

IT    RM2005A000443    * 12/2005    .............. A61P 27/02

OTHER PUBLICATIONS

Foreign priority document Italy RM2005A000443, received at International Bureau on Nov. 23, 2006.*
Picton et al., Carbohydrate Polymers, 2000, 42, p. 23-31.*
Ubels John L. et al.; "Effects of preservative-free artificial tear solutions on corneal epithelial structure and function"; Archives of Opthalmology; vol. 113; No. 3; 1995; pp. 371-378; XP009091340; ISSN: 0003-9950.

* cited by examiner

*Primary Examiner* — Shaojia Anna Jiang
*Assistant Examiner* — Jonathan S Lau
(74) *Attorney, Agent, or Firm* — Arent Fox LLP

(57) ABSTRACT

Ophthalmic solutions containing arabinogalactans with a protective activity on the corneal epithelium, particularly suitable for use as artificial tears stimulating the recovery of corneal lesions and also particularly useful for contact lens users, containing from 1% to 10% by weight of arabinogalactan in an aqueous solution and possible other excipients, among which tonicity-adjusting agents, pH correctors, buffers and preservatives, except for benzalkonium chloride.

The compositions according to the invention have a virtually negligible viscosity, but are sufficiently mucoadhesive to assure a considerable permanence time in the area of application. Besides being well-tolerated, the aforesaid compositions have considerable re-epithelization capacity.

27 Claims, 5 Drawing Sheets

OPHTHALMIC COMPOSITIONS CONTAINING MUCOADHESIVE POLYSACCHARIDES ABLE TO PROMOTE CORNEAL RE-EPITHELIZATION

CROSS-REFERENCE TO RELATED APPLICATION

This application is a National Stage entry of International Application No. PCT/IT2006/000616, filed Aug. 10, 2006, the entire specification claims and drawings of which are incorporated herewith by reference.

DESCRIPTION

The present invention concerns ophthalmic compositions containing mucoadhesive polysaccharides able to promote corneal re-epithelization. More specifically, the invention concerns ophthalmic solutions containing arabinogalactans having a protective action on the corneal epithelium, which are particularly recommended for use as artificial tears for stimulating the recovery of corneal lesions, and particularly useful for people wearing contact lenses.

As is known, the cornea is the anterior section of the fibrous tunic of the eyeball, of which it constitutes only a sixth part since the remaining portion is made up of the sclera—the two structures being in continuity as well as contiguity. In fact, the cornea has a lesser curvature compared to that of the sclera, so that it appears slightly protruding forwards. Due to its peculiar characteristics of transparency and avascularity, and for its shape, which makes it a perfect concave-convex lens, the cornea constitutes an essential element of the ocular dioptric system.

Its anterior surface, convex and elliptical, has a horizontal diameter slightly higher than the vertical one, and thus it has a different curvature in these two directions. This difference causes physiological astigmatism. The posterior surface is concave and circular, and instead has the same diameter and radius in all directions. Corneal thickness ranges between approximately 0.5 mm in the central region to approximately 0.7 mm in the peripheral region.

Histologically, the cornea is made up of five layers, which are as follows from the outside inwards: the epithelium, Bowman membrane, the stroma, Descemet membrane and the endothelium.

The cornea carries out its optical function thanks to a perfect transparency and to the evenness of its contact surface with the air. The latter feature is due to the presence of the lachrymal film (tear film) covering the epithelium, which is per se rough due to the presence of a meshwork of microplies in the external layer. The tear film makes the epithelium smooth, uniform and of high optical quality.

The tear film, which also covers the bulbar conjunctiva and palpebral conjunctiva, is composed of three overlapping layers, which are as follows from the external one inwards: the lipid layer, the aqueous layer and the mucous layer. The mucin produced by the goblet cells of the conjunctival epithelium makes the whole epithelial surface smooth, enabling the uniform distribution of the aqueous component of the film on it; the lipid layer, secreted by the meibomian and Zeis glands, has the function of preventing tear film evaporation.

As already noted, transparency is the fundamental property of the cornea. It is made possible by the absolute avascularity of this tissue, the structural characteristics of the stroma and by certain specific physiological processes governing the aqueous turnover and deturgescence of the cornea itself and prevent its imbibition, maintaining the hydration rate to a normal value of about 78%.

Other physiological characteristics of the cornea are its specularity (light reflection on its surface), which is linked to epithelial integrity, and permeability—an essential function for the aqueous turnover and/or the penetration of foreign substances such as drugs.

The considerable sensitivity to stimuli of various kinds is linked, finally, to the great innervation of the membrane, which decreases in old age and in the presence of some phlogistic and dystrophic-degenerative alterations.

The corneal alterations most commonly found may represent the initial symptoms of processes of a flogistic, dystrophic or degenerative nature, or an evident state of disease. Among the alterations of a mechanical-traumatic nature there are: corneal abrasions, due to a superficial rubbing of the corneal epithelium or to contact with foreign bodies, such as metal, glass or plastic particles, wood or plant residues; lacerations and perforations due to objects entering the eye with particular force and which penetrate in some depth; recurrent corneal erosions, which consist of spontaneous episodes of breakage or scaling of the corneal epithelial layers; burns caused by weak acids or weak bases, heat or ultraviolet radiation.

Destruction of the corneal epithelium in any way increases the risk of invasion on the part of pathogens, with potentially devastating results. The conjunctiva is, in fact, one of the body's tissues colonized by microbes right from the very first moments of extrauterine life, and it must be noted that among the habitual resident microorganisms, such as streptococci (*St. viridans*), staphylococci (*S. epidermidis, S. aureus*), haemophiles, *Propionibacterium acnes*, there are some which have all the characteristics to be considered as true pathogens.

The conjunctival ecosystem is a system that tends to be balanced and biologically active, and remains as such as long as tissue, microbes or environmental factors do not arise which disrupt this equilibrium, thereby making the conjunctival habitat a favourable terrain for microbes or for the host. The tissue factors are dependent on the histological structure of the conjunctival tissue and on the secretions making up the lachrymal film: these factors can act as co-causes in the pathogenesis of various corneal infections brought about by bacteria, viruses and mycetes. These can invade the corneal tissue, especially in the presence of corneal lesions, and give rise to keratitis of even a very serious and disabling kind that can lead to corneal ulcer. Bacterial keratitis is characterised by acute pain, ulceration of the epithelium and, sometimes, of the corneal stroma, as well as conjunctival secretion. The ethiological agents of this type of ocular lesions are: *S. aureus, St. pneumoniae, Ps. aeruginosa, Citrobacter, Klebsiella, Enterobacter*. Moreover, *Mycobacterium chelonei* and *Mycobacterium fortuitum* can cause chronic corneal ulcerative lesions. As regards ethiological agents of a mycotic type, mycotic keratitis is caused mainly by filamentous saprophyte mycetes and yeasts that colonise on the corneal epithelial lesions. Finally, keratitis due to *Acanthamoeba* is a rare form of chronic keratitis caused by this parasite—which can even threaten eyesight—and is characterized by a ring-shaped multifocal suppuration of the corneal stroma in subjects presenting previous ulcerations.

All corneal alterations (whether of the traumatic, phlogistic or degenerative type) which cause tissue destruction or loss of substance are quickly repaired through physiological mechanisms that differ in part from those of other tissues because of the avascularity of this membrane. The healing process, which is influenced by the characteristics of the lesion and is certainly more problematic in the presence of septic ulcerations, always starts at the epithelial level, not only in case of superficial damage limited to this layer, but also in cases affecting the parenchyma. That is, there is an interaction of the epithelium in the healing of stromal lesions that may be exemplified as the formation of an "epithelial cap" necessary for regulating the development of the subsequent phenomena of collagen regeneration.

Mere epithelial wounds or abrasions are repaired rapidly thanks also to the marked mitotic activity of the cell elements in this region. Actually, at the moment of the trauma, there occurs a temporary interruption of the physiological mechanism of surface cell scaling and a shift and migration of intact adjacent cells to the damaged area. The interruption ceases when the deficient area is completely covered and the regeneration of the epithelial elements assures the restoration of the normal structural characteristics.

If the alteration is epithelial, its complete recovery guarantees the restoration of perfect membrane specularity and transparency.

A particular and not rare cause of corneal abrasions is contact lenses. The causes of abrasion may involve different factors of a physiological, toxic or mechanical kind, and the corneal abrasions induced by contact lenses can be due, in particular, to their use, to difficulties in their insertion and removal, problems of lens-cornea relations, damaged lenses or to foreign bodies trapped under a lens. These abrasions may derive from using both rigid and soft lenses, but they are more common in users of rigid lenses. A study conducted on 500 users of soft contact lenses showed that a third of them had rather serious problems with their eyes that could result in infections, and that almost 50% of them had signs of mild lesions on at least one eye (R. J. Derick et al., *CLAO J.*, 1989 October-December; 15(4):268-70).

Corneal abrasions are thus a problem that may affect anyone, but contact lenses undoubtedly cause friction on the cornea, and this increases the likelihood of the occurrence: users of contact lenses suffer from corneal lesions about three times as much as non-users.

The use of contact lenses may also produce a series of other problems deriving from their interference with normal oxygen supply to the corneal epithelium or from pathological conditions, such as giant-papillary conjunctivitis or corneal vascularization, or the more common case of dry eye syndrome. The latter, also known as "dry eye" or keratoconjunctivitis sicca, is a disorder caused by a decrease in the amount and quality of tears. The typical symptoms of the pathology are an irritation and burning sensation of the eyes, the feeling of grit or foreign bodies, photophobia, pain and visual haze. In the long run there may be ulcerations compromising eyesight itself.

To treat dry eye or reduce its related symptoms, many artificial tear fluid formulations have been introduced, to be applied periodically by instillation on the cornea (or in the conjunctival fornix) in order to provide a tear fluid substitute and alleviate the dryness sensation in the eyes. To increase the permanence time on the corneal surface and also have a good tolerability, these preparations are generally made viscous by adding agents of high molecular weight—normally hydrosoluble polymers of synthetic, semi-synthetic or natural origin. On the assumption that, in order to have a high pre-corneal permanence time, a tear fluid substitute must have properties as close as possible to those of mucin dispersions, that is, it must behave as much as possible like a mucomimetic substance, the preference has been given to compositions based on macromolecular compounds of natural origin such as cellulose derivatives (in particular, cellulose esters like carboxymethylcellulose, and alcohol derivatives of cellulose ethers like hydroxypropylmethylcellulose), glycosaminoglycans (in particular, hyaluronic acid, a polysaccharide present in many human and animal tissues and fluids, and widely used in ophthalmic preparations), polysaccharides having suitable rheological properties (such as polysaccharide extracted from tamarind gum, TSP).

Moreover, in order to be able to present the required lubricating properties of the corneal surface, these tear fluid substitutes always have a certain viscosity (even if, in preferred solutions, this viscosity decreases drastically when the product is subjected to a shear stress, as in the case of blinking), and may involve eyesight hazing as well as leave residues on the cornea or on the edge of eyelids.

In the case of the aforesaid problems related to contact lens use, it is instead extremely important for a possible product used as a tear fluid supplement to have a low viscosity—besides being well-tolerated and having no irritant effects on the eye—so as not to blur vision or leave residues on the lens and on eyelid rims. Equally important for such a product is to be able to assure corneal epithelial integrity and prevent any negative interactions and/or reactions with the contact lens material.

The scientific publication by John L. Ubels et al. J. L. Ubels et al. "Effects of preservative-free artificial tear solutions on corneal epithelial structure and function", *Archives of Ophthalmology*, vol. 113, No. 3 1995, 371-378) discloses preservative-free bicarbonate-containing artificial physiologic tear solutions. Such solutions are suggested to be beneficial in providing comfort for patients with mild to moderate dry eye but also to promote recovery of the damaged corneal epithelial barrier, which can occur with dry eye, other ocular surface diseases or excess use of preserved ophthalmic solutions.

According to the present invention, it has been found that ophthalmic solutions containing particular natural polysaccharide polymers, arabinogalactans, formulated so as to have a virtually negligible viscosity, possess sufficient mucoadhesiveness to avoid being drained away in a short time from the corneal surface and, besides being well-tolerated, possess a notable capacity to promote re-epithelisation. It has, in fact, been demonstrated, within the frame of the studies connected with the present invention, that these compositions—applied on eyes with a damaged epithelium—accelerate recovery. As a result, the proposed compositions, associated with contact lens use, are able to stimulate the healing of corneal abrasions that may arise, preventing the aggravation of epithelial damage and any complications. As already mentioned, another important characteristic of the product, which makes it innovative and ideal for the purpose, is that—although possessing suitable mucoadhesive properties—it does not alter the viscosity of aqueous solutions, and thus does not interfere with vision both in subjects wearing contact lenses and in non-users. At the same time, the mucoadhesive properties allow the product to establish bonds of various kinds with the mucous lining the conjunctival and corneal surface of the eye, and these bonds enable a greater permanence of the product in the pre-ocular region, and thus the possibility of performing the re-epthelisation and hydrating activity characterizing the product.

Ophthalmic solutions for use as artificial tears containing arabinogalactan as corneal surface lubrication polymer are already described in U.S. Pat. No. 4,039,662 (Hecht et al., assigned to Alcon Laboratories Inc.). In this case, however, the re-epithelisation properties of the polysaccharide were not highlighted or exploited and, above all, its usability was conditioned to the necessary presence of benzalkonium chloride in the formulation. According to the description of this document, in fact, the incorporation of benzalkonium chloride—a substance already used in ophthalmic compositions as a biocide—is a critical element for the preparation proposed, because it is thought that this compound, combined with, or forming complexes with, the polysaccharide, is the cause of the product's permanence in an adsorbed state on the corneal surface, so as to perform its function as a pre-corneal film stabilizer. In line with this observation, the cited document proposes ophthalmic solutions based on arabinogalactan and containing benzalkonium chloride as a necessary ingredient.

According to the studies carried out in the frame of the present invention, on the other hand, the re-epithelisation and protective properties of the corneal surface shown by arabinogalactans, as well as their mucoadhesive properties giving them a high permanence time in the pre-corneal film, even in the absence of any significant viscosity, are not in any way conditioned by the co-presence of benzalkonium chloride. Therefore, the re-epithelising compositions containing arabinogalactans according to the present invention rule out the presence of benzalkonium chloride since they can make use of many other products suitable for the purpose should the composition require the inclusion of preservatives.

As is known, arabinogalactans are a class of long-chain, densely branched polysaccharides with a molecular weight ranging between 10,000 and 120,000 daltons and a central structure consisting of a chain of galactopyranose units. In nature they are found in various microbe systems, especially Mycobacteria, where they are complexed with peptidoglycan and mycolic acid to form the cell wall. Many edible and non-edible plants are rich sources of arabinogalactans, mainly in a glycoproteic form. Many herbs with acknowledged immuno-stimulant properties, such as *Echinacea purpurea, Baptisia tintoria* and *Thuja occidentalis*, contain significant quantities of arabinogalactans. The woody tissues of plants of the *Larex* genus are particularly rich in arabinogalactans, especially *Larex occidentalis*, but also *Larex dahurica* (original from Central Asia), for example, *Larex dicidua* (European) and *Larex leptolepis* (Japanese). In fact, larch wood is the most common industrial source of arabinogalactan, from which source this polysaccharide is extracted to be used not only for industrial purposes, such as in the cosmetics industry, but also—and above all—in the food industry, as a dietetic and nutritional ingredient rich in fibre, in beverages and also as an immunomodulating agent.

Therefore, the present invention specifically provides an ophthalmic composition for use in a method for the treatment of keratoconjuctival lesions and inflammations i.e as a tear fluid substitute having a keratoprotective activity and re-epithelising activity, consisting of an aqueous solution containing between 1% and 10% by weight of arabinogalactan and not containing benzalkonium chloride. The most suitable concentrations of arabinogalactan for the use proposed according to the present invention are, specifically, the concentrations ranging between 3% and 5% by weight of polysaccharide, in an aqueous solution.

According to the preferred embodiments of the present invention, the arabinogalactan used in the compositions proposed is arabinogalactan from larch of pharmaceutically acceptable grade. In particular, the arabinogalactan preferentially used in the preparations according to the present invention (arabinogalactan CAS#9036-66-2) has the commercial name of FiberAid® AG and is produced by the LAREX® company (Cohasset, Minn., USA) in accordance with U.S. Pat. No. 5,756,098. This arabinogalactan is in the form of a fine white powder (molecular weight=45 kdalton), dispersible but not completely soluble in cold water.

All the arabinogalactans isolated from larch are nitrogenless polysaccharides. One third of the molecule is composed of the main chain, of the (1→3)-β-D-galactopyranan type, while the rest consists of lateral groups bonded in position (1→6) to each galactose unit, whose size varies from monosaccharides to olygosaccharides. The distribution of the lateral groups is not uniform. Often, the lateral group is the disaccharide β-D-Galp-(1→6)-β-D-Galp or β-L-Arap-(1→3)-α-L-Araf. Less frequently, there is the monomer β-D-Galp or the monomer α-L-Araf. The galactose and arabinose units are in a molar ratio of approx. 6:1.

Morphological studies on arabinogalactan have shown that this polymer has great conformational freedom and may take on many distinct shapes, but the main chain generally has a rigid triple spiral helix structure while the lateral groups form flexible branches with many exposed hydroxy groups (R. Chandrasekaran, S. Janaswamy, 2002, *Carbohydrate Research*). This is considered to be the reason underlying the mucoadhesive characteristics of the polymer, which makes it able to establish hydrogen bonds with the mucin molecules of the eye.

According to some specific embodiments of the present invention, the ophthalmic composition contains—besides arabinogalactan—also one or more tonicity-adjusting agents that give the solution the desired osmolarity value. Since the proposed ophthalmic solution may be isotonic or slightly hypotonic with respect to tear fluid, the tonicity-regulating agents will be present in the composition in such a quantity to provide a solution with an osmolarity ranging between 150 and 300 mOsm/L. Preferably, the said one or more tonicity regulating agents are chosen from the group consisting of: mannitol, sodium chloride, potassium chloride, dextrose, boric acid and sorbitol.

Since arabinogalactan turned out to be stable also in aqueous solutions buffered at various pH values, other ingredients that can be added, similarly to what is already known in the pharmaceutical field, are one or more ophthalmically accepted acids or bases, as pH correctors, and/or one or more buffers. In particular, the usable buffers may be chosen from the group consisting of: phosphate buffer, borate buffer, citrate buffer, bicarbonate buffer, trizma buffer (tri-hydroxymethyl-amminomethane). Further, other buffer systems can be advantageously used in the compositions according to the invention.

When the product is not packaged in monodose units, the composition can also include preservatives and antimicrobics, except for benzalkonium chloride. Possible preservatives that are compatible with the product are, in particular, sodium merthiolate or timerosal, phenylmercuric nitrate or acetate, phenylethyl alcohol, methyl-, ethyl- and propylparaben, chlorhexidine acetate or gluconate and chlorobutanol.

Finally, even chelating agents like the edetates or EDTA can be added, when required, to the compositions containing arabinogalactans according to the invention.

According to another aspect thereof, the present invention also provides the use of an ophthalmic solution composition containing between 1% and 10% weight, and preferably between 3% and 5% by weight, of arabinogalactan in aqueous solution and not containing benzalkonium chloride for the production of an ophthalmic composition an artificial tear solution for the treatment of keratoconjuctival lesions an inflammations, i.e. with having a keratoprotective and re-epithelising activity. As already noted, the formulation of the said ophthalmic composition can rule out the use of benzalkonium chloride with no problem whatsoever.

More specifically, the ophthalmic composition realized with the use of arabinogalactan according to the teachings of the present invention is a tear fluid substitute indicated for contact lens users. According to some specific embodiments, the said ophthalmic composition is a tear fluid substitute indicated for the treatment of keratoconjuctival lesions and inflammations and, in the latter case, may be more specifically an ophthalmic composition recommended for the treatment of corneal abrasions caused by contact lens use.

Some examples of arabinogalactan-containing compositions usable as tear fluid substitutes with a keratoprotective and re-epithelising activity according to the invention are presented below, by way of non-limiting examples.

| Composition 1 | |
|---|---|
| arabinogalactan | 2% w/w |
| mannitol | q.s. to 300 mOsmol/kg |
| phosphate buffer pH 7.4 | q.s. to 100% w/w |
| Composition 2 | |
| arabinogalactan | 3% w/w |
| mannitol | q.s. to 300 mOsmol/kg |
| deionised water | q.s. to 100% w/w |
| Composition 3 | |
| arabinogalactan | 6% w/w |
| NaCl | q.s. to 300 mOsmol/kg |
| deionised water | q.s. to 100% w/w |
| Composition 4 | |
| arabinogalactan | 2% w/w |
| mannitol | q.s. to 300 mOsmol/kg |
| phenylmercuric nitrate | 0.002% w/w |
| phosphate buffer pH 5.9 | q.s. to 100% w/w |
| Composition 5 | |
| arabinogalactan | 5% w/w |
| NaCl | q.s. to 300 mOsmol/kg |
| Sodium merthiolate | 0.008% w/w |
| deionised water | q.s. to 100% w/w |

For the preparation of the aforesaid compositions, a quantity of accurately weighed polymer was dispersed in deionised water or phosphate buffer and kept under stirring until it is completely dissolved. Suitable quantities of the other excipients (mannitol, NaCl and/or preservative) were added to the solution thus obtained, still under stirring until they were completely dissolved.

The compositions thus obtained can be sterilized by filtering through a 0.22 µm membrane.

The specific characteristics of the present invention, as well as its advantages, will be more evident with reference to one of its specific embodiments described below merely for exemplificative purposes, together with the results of the experiments carried out on them and with the data for comparisons with the prior art. Some experimental results are also illustrated in the figures of the attached drawings, wherein.

Figure 5:
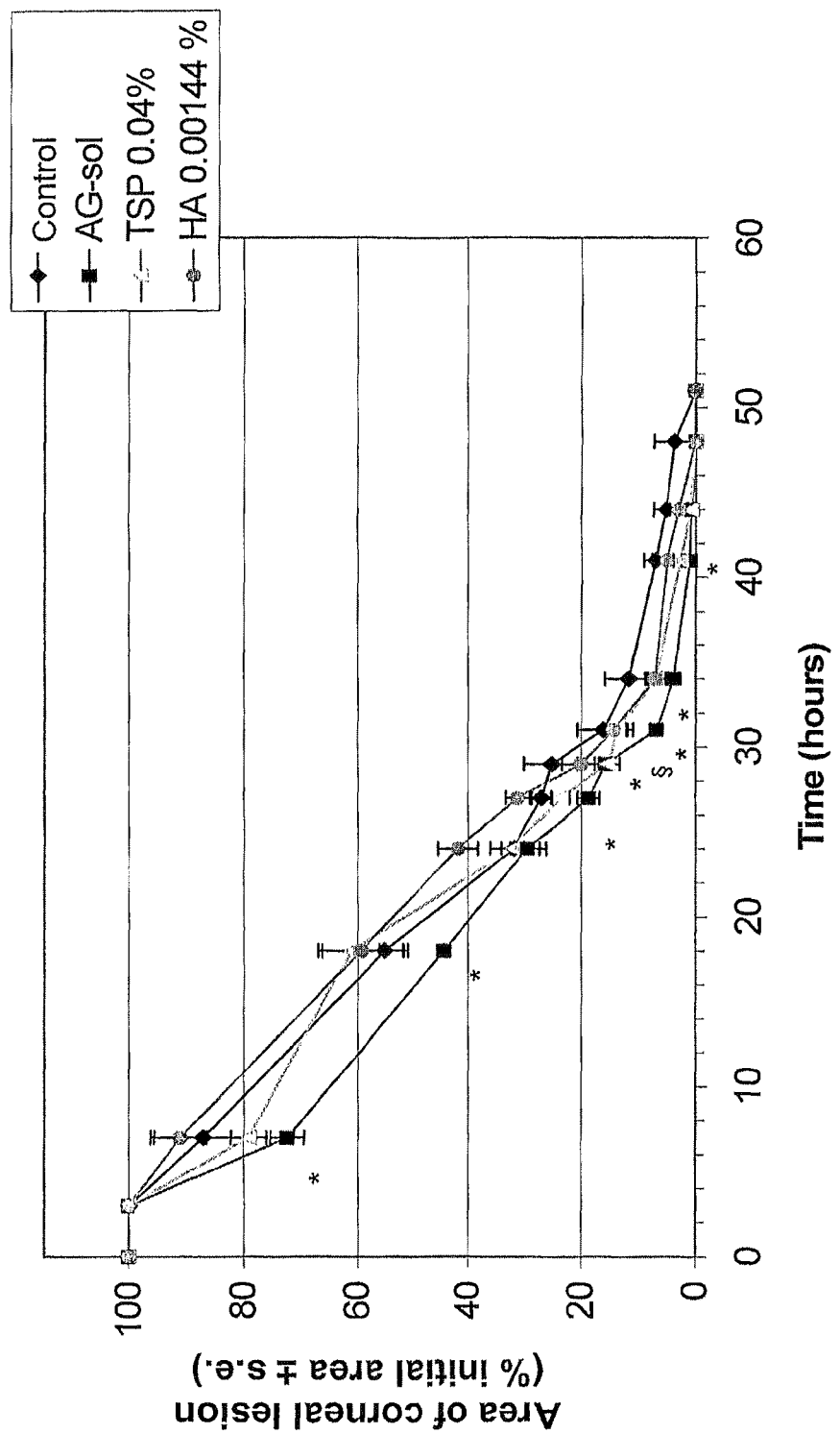
Figure 6:
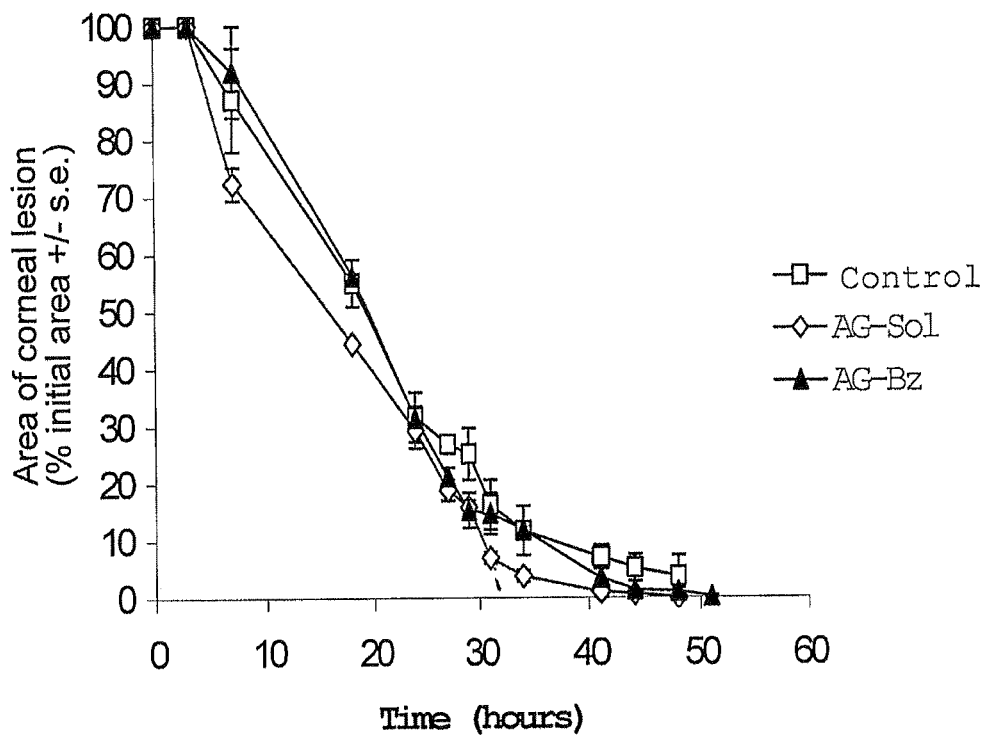
Figure 6A:
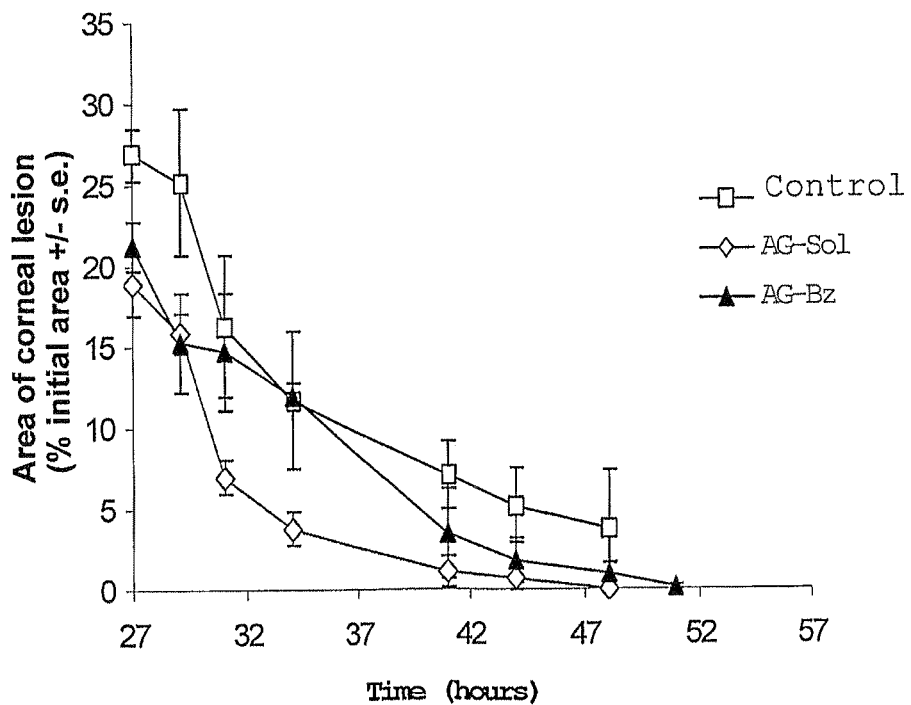
Figure 7:
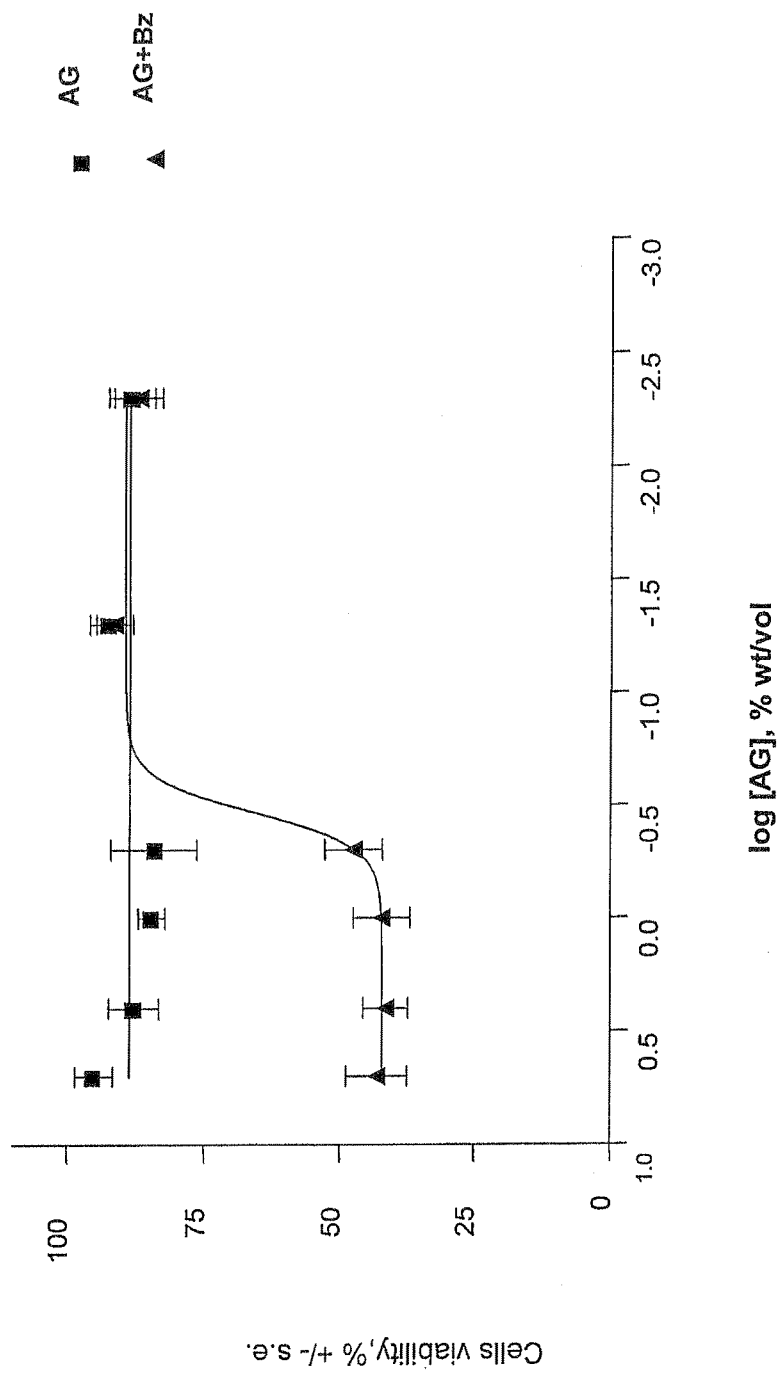

FIG. 5 graphically reports the results of a recovery test of a corneal lesion experimentally induced in rabbits, which were then treated with the composition according to the invention (AG) or, for comparison, with tamarind gum saccharide (TSP) or with hyaluronic acid (HA);

FIGS. 6 and 6a graphically report—on two levels of detail—the results of a recovery test of the corneal lesion experimentally induced as in the tests of FIG. 5, wherein the comparison is made between the composition of the present invention (AG-Sol) and a similar solution also containing benzalkonium chloride (AG-Bz); and FIG. 7 shows the results of cell toxicity tests in terms of cell vitality after exposure to a solution containing arabinogalactan according to the invention (AG-Sol), or to a similar solution also containing benzalkonium chloride (AG-Bz).

Viscosity Tests

Figure 1:
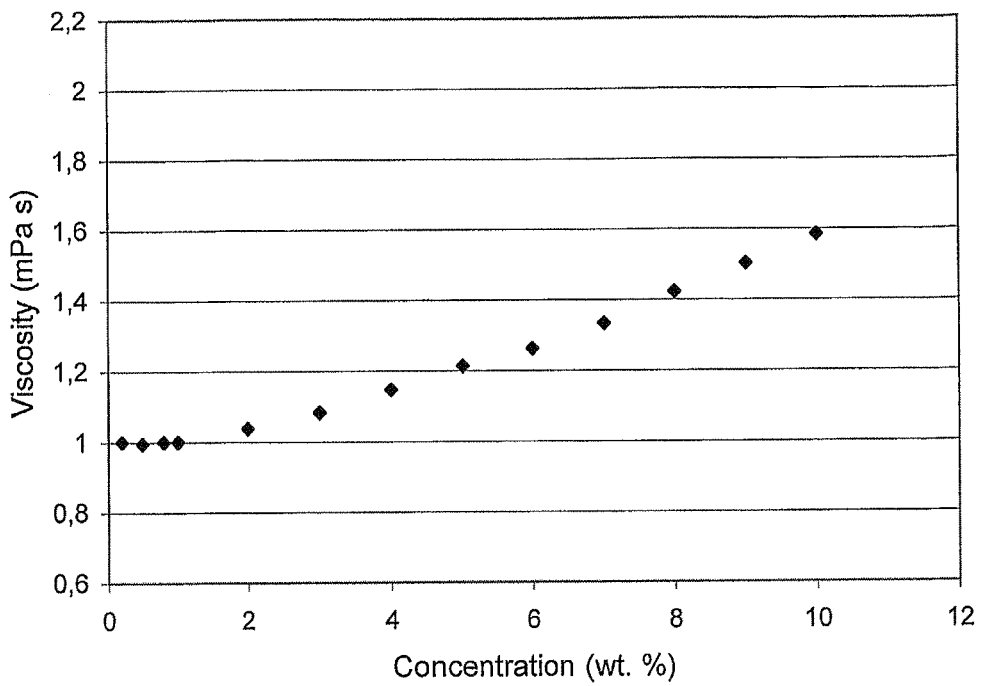
FIG. 1 shows the variation in viscosity of the compositions containing arabinogalactan in aqueous solution according to the present invention as the concentration in polysaccharide varies.

Arabinogalactose solutions (FiberAid® AG of LAREX®, Cohasset, Minn., USA), hereinafter called AG, in various concentrations (0.2, 0.5, 0.8, 1, 2, 3, 4, 5, 6, 7, 8, 9 and 10% by weight) were subjected to viscosity tests by using a Rheostress RS 150 (Haake) rotational viscosimeter with coaxial cylinder measurement bodies (Z40 and Z41), at a constant temperature of 25° C. The viscosity values of the solutions are reported graphically in FIG. 1 of the attached drawings.

The rheograms were carried out for velocity gradient values ranging between 0 and 200 sec$^{-1}$ and, from the graphs, the correlation between shear stress ($\tau$) and velocity gradients ($\gamma$) was assessed by mathematical processing using Rheowin software. It was thus found that the solutions of the AG product have a Newtonian rheological behaviour and do not present thyxotropy.

The Newtonian behaviour of the AG solutions is due to their non-viscosity—a desirable characteristic in the case of solutions to be applied to the eye when wearing contact lenses, so that the liquid penetrating into the space between lens and cornea does not cause any haziness of vision.

Mucoadhesion Tests

1. Mucoadhesion Tests on Solid Matrix

The mucoadhesive properties of arabinogalactan according to the invention (FiberAid® AG, Larex®) were assessed by measuring the force required to separate two mucous surfaces between which the sample under examination was placed. The mucous surfaces were composed of an aqueous dispersion of 25% pig gastric mucin (TCI, Tokyo) adsorbed on filter paper (Saettone et al., 1989, *Int. J. Pharm.*, 51:203-212).

The equipment used consists of a micrometric scale, a mobile platform and computerized system able to record the force necessary to detach the two surfaces (sample under examination and mucous layer) as a function of the elongation (software TP 5008, TiePie Engineering, Leeuwarden, Netherlands).

The adhesion work was measured for solid matrices consisting of the polysaccharide polymer under examination, of 13 mm diameter and 1 mm thickness, that were prepared by compressing a suitable quantity of polymer material by means of a hydraulic press (Perkin-Elmer) at a pressure of 3,000 kg/cm$^2$.

The results obtained were compared with the adhesion work measured by solid matrices of the same size with TS-polysaccharide (TSP), already known in the literature as mucoadhesive, prepared with the same method. The results obtained are reported in the following Table.

TABLE 1

Adhesion work for the polymers under study (mean ± S.E., n = 20)

|  | AG | TSP | mucin/mucin |
|---|---|---|---|
| Adhesion work (erg/cm$^2$) | 282.77 | 355.87 | 118.00 |
| S.E. | 23.60 | 41.73 | 9.00 |

2. Rheological Evaluation of the Strength of the Mucin-Polymer Adhesion Bond

To examine the mucoadhesive properties of arabinogalactan (AG) in more detail, the method of Saettone et al. (Saettone et al., 1994, *Journal of Ocular Pharmacology*, 10:83-92) and Hassan and Gallo (Hassan, Gallo, 1990, *Pharm. Res.*, 7:491-495) was followed, consisting of measuring the viscosity variations caused in a mucin dispersion after adding the polymer. According to this method, the viscosity component due to bioadhesion, $\eta_b$, was calculated by the equation $\eta_b = \eta_t - \eta_m - \eta_p$, where $\eta_t$, $\eta_m$ and $\eta_p$ are individual coefficients of viscosity of the system, mucin and polymer, respectively. The value of $\eta_b$ was subsequently normalized according to the following equation: $\Delta\eta/\eta = \eta_b/\eta_p$.

Then, the measures of viscosity variations due to mucin-polymer interaction were carried out on aqueous solutions containing: i) 15% of mucin alone ($\eta_m$); ii) AG and other polymers, used as reference, at their respective effective concentrations ($\eta_p$); iii) mucin-polymer mixtures, at the same concentrations previously indicated ($\eta_t$).

The compositions used were as follows:

1. Aqueous solution of pig gastric mucin (MGS; TCI, Tokyo), at 15% w/w;

2. Aqueous solution of AG, at 5% w/w (FiberAid® AG, LAREX®);

3. Aqueous solution of TSP, at 0.5% w/w (Farmigea, Pisa);

4. Aqueous solution of hyaluronic acid, at 0.2% w/w (Chemofin, Milano);

5. Aqueous dispersion of mucin, at 15% w/w, and AG at 5% w/w;

6. Aqueous dispersion of mucin, at 15% w/w, and TSP at 0.5% w/w;

7. aqueous dispersion of mucin, at 15% w/w, and hyaluronic acid at 0.2% w/w.

The viscosimetric measures were carried out by means of a Rheostress RS 150 (Haake) rotational viscosimeter with coaxial cylinder measurement bodies (Z40 and Z41), at a constant temperature of 32° C. The rheograms were obtained for velocity gradient values ranging between 0 and 500 sec$^{-1}$.

The polymeric solutions show a Newtonian behaviour, and the graphs obtained were used in order to evaluate the linear correlation between shear stress ($\tau$) and velocity gradients (indicated with a $\gamma$ or D) by means of mathematical processing performed with the Rheowin software.

Hyaluronic acid, mucin and mucin-polymer dispersions show a pseudoplastic behaviour. The mathematical correlation of the graphs obtained, performed with the Rheowin software, is as follows: $\tau = aD^b$. The viscosity in the Newtonian formulations and the apparent viscosity of the pseudoplastic formulations were calculated by choosing a certain value of D and then obtaining $\tau$ from the respective equations (D=200 s$^{-1}$).

The viscosity values for all the compositions are reported in Table 2 below, while the values of parameter $\Delta\eta/\eta$ for the polymers used are reported in Table 3.

TABLE 2

Viscosity of the compositions under study

| Composition | MGS (% w/w) | AG (% w/w) | TSP (% w/w) | Hyaluronic acid (% w/w) | $\eta$ (mPa·s) |
|---|---|---|---|---|---|
| 1 | 15.0 | — | — | — | 47.98 |
| 2 | — | 5.0 | — | — | 1.38 |
| 3 | — | — | 0.5 | — | 9.16 |
| 4 | — | — | — | 0.2 | 24.40 |
| 5 | 15.0 | 5.0 | — | — | 73.10 |
| 6 | 15.0 | — | 0.5 | — | 190.41 |
| 7 | 15.0 | — | — | 0.2 | 145.97 |

TABLE 3

$\Delta\eta/\eta$ of the compositions under study

| Composition | MGS (% w/w) | AG (% w/w) | TSP (% w/w) | Hyaluronic acid (% w/w) | $\Delta\eta/\eta$ |
|---|---|---|---|---|---|
| 5 | 15.0 | 5.0 | — | — | 17.21 |
| 6 | 15.0 | — | 0.5 | — | 14.55 |
| 7 | 15.0 | — | — | 0.2 | 3.02 |

As the results show, the aqueous solution of AG at 5% w/w presents a much lower viscosity (1.38 mPa·s) than the polymers taken as reference (9.16 mPa·s and 24.40 mPa·s for TSP and for HA, respectively), while the normalized value $\Delta\eta/\eta$ of AG is of the same magnitude as the TSP value. This indicates that AG is able to form interactions of various kinds with the mucous covering the conjunctival and corneal surfaces of the eye. Therefore, although being a non-viscous polymer that does not blur vision and does not interfere with contact lens use, AG establishes interactions enabling a prolonged permanence of the product in the pre-ocular region and thus a prolonged protection and hydration of the corneal surface.

Studies of Contact Lens-Polymer Interaction

To assess the degree of interaction of contact lenses with the polymer under study, a fluorescent derivative of arabinogalactan (FITC-AG) was prepared, as reported below.

An accurately weighed quantity of arabinogalactan (FiberAid® AG, Larex®) equal to 1 g was dissolved in 10 ml of dimethylsulfoxide containing a few drops of pyridine. To this solution was added 0.1 g of fluorescein isothiocyanate (Sigma-Aldrich, Germany) followed by 20 mg of dibutyltindilaurate (Sigma-Aldrich, Germany). The mixture thus obtained was heated for two hours at 95° C. After precipitation and washing with ethanol to remove the products that did not react, the FITC-AG was filtered and dried at 80° C. (A.N. de Belder & K. Granath, 1973, *Carbohydrate Research*, 30:375-378).

The following solutions in deionised water were prepared for the test:

1. FITC-AG 5% w/w;

2. sodium fluorescein (SF) (Sigma-Aldrich, St. Louis, USA) 0.0223% w/w.

The concentration of the SF solution was chosen so as to have the same fluorescence as the FITC-AG solution at 5% w/w. Soft daily contact lenses (Focus Dailies®, Ciba Vision, Germany) were used for the test.

The contact lenses were immersed in 1 ml of artificial tear fluid without proteins, to which had been added 50 μl of a solution of FITC-AG at 5% w/w or of SF at 0.0223% w/w, and left to rest for 30 minutes. The lenses were then washed by immersing them in 100 ml of artificial tear fluid for 15 minutes under slow stirring with a magnetic stirrer. The treated lenses were then observed with a Wood lamp at 365 nm in comparison with untreated contact lenses as a reference.

None of the lenses showed any visible traces of fluorescence, demonstrating the fact that the AG polymer is not withheld on the lens surface in the conditions employed.

The artificial tear fluid had the following composition expressed in mg/100 ml of deionised water: $MgCl_2$ 4.75; $CaCl_2$ 7.97; $KHCO_3$ 260.00; NaCl 754.00 (Burgalassi et al., 1999).

Ferning Test

The innermost layer of lachrymal fluid is composed of mucous glycoproteins, which in normal conditions are produced by goblet cells of the conjunctiva. One of the most important physical characteristics of the mucous is its capacity to crystallize in fernlike forms when it is made to evaporate at room temperature.

The various aspects of tear mucous crystallization can yield useful indications on the conditions of stability of lachrymal film, and they are classified into four types:

Type I: ferning is present in a uniform manner without any spaces between individual ferns. The ferns are large and densely branched.

Type II: crystallisation in the form of ferns is still abundant but the individual ferns are smaller in size and are not as widely branched. There are appreciable spaces between the ferns.

Type III: ferning is present in a partial way, the ferns are small and poorly branched; there are considerable spaces between the ferns.

Type IV: ferning is absent and there are filaments or conglomerates representing the degenerated mucous material mixed with exfoliate cells.

The first two kinds of ferning are typical of normal eyes with good conditions of the mucous layer and of the lachrymal film. Type III seems to be a form of transition and indicates a difficult state of the mucous in maintaining its integrity and functions. Type IV indicates a great alteration of the lachrymal fluid mucous components.

All the ophthalmic solutions that crystallize in the form of ferns comparable to type I and type II are structurally similar to the mucous glycoproteins produced by the conjunctival goblet cells.

Thus, the ferning test was carried out in order to evaluate the possible capacity of AG to crystallize with characteristics similar to the mucous present on the eye surface. The test consists of evaporating at room temperature (25±1° C.), for 24 h, on a microscope slide, a previously prepared mixture composed of 10 μl of solution at 2.5% w/w of AG and 2 μl of artificial tear fluid.

The 2.5% AG solution was prepared by dispersing, under stirring, a suitable quantity of polymer (FiberAid® AG, Larex®) in deionised water. After evaporation, the residue was observed by means of a polarized light Reichert-Jung Microstar microscope with a 10× magnifying lens.

The crystallization of the AG solution produced fern-like branched structures very similar to those obtained with human tear fluid. The result obtained, also confirmed by rheological interaction tests, supports the hypothesis that the polymer under study is compatible with the glycoprotein structures of the ocular mucous. It may thus be hypothesized that it can replace the natural mucous component when the latter is deficient due to pathological reasons.

Biological Tests

1. Evaluation of the Pre-Corneal Permanence Time

The present study used the fluorescent derivative of arabinogalactan (FITC-AG), prepared as already described in the section on the contact lens-polymer interaction studies.

The quantitative determination of FITC-AG in biological samples was carried out through fluorimetric analysis. The equipment was composed of a Shimadzu RF-551 fluorescence detector with appropriate integration software. The detection was performed at an excitation wavelength of 490 nm and emission wavelength of 514 nm.

The test was carried out on New Zealand albino rabbits weighing 2-2.5 kg. 50 μl of the aqueous composition FITC-AG 5% w/w was administered to the lower conjunctival sac of the rabbits. At suitable time intervals after instillation (1, 3, 5, 10, 20, 30, 45 and 60 minutes), tear fluid samples (1.0 μl) were collected from the marginal portion of the lower conjunctival sac by means of microcapillary (Microcaps, Drummond Scientific, NJ, USA), avoiding any contact with the corneal epithelium. The tear fluid samples were transferred to Eppendorf test tubes and then analysed by means of fluorimetric analysis after dilution with 50 μl of water.

Figure 2:
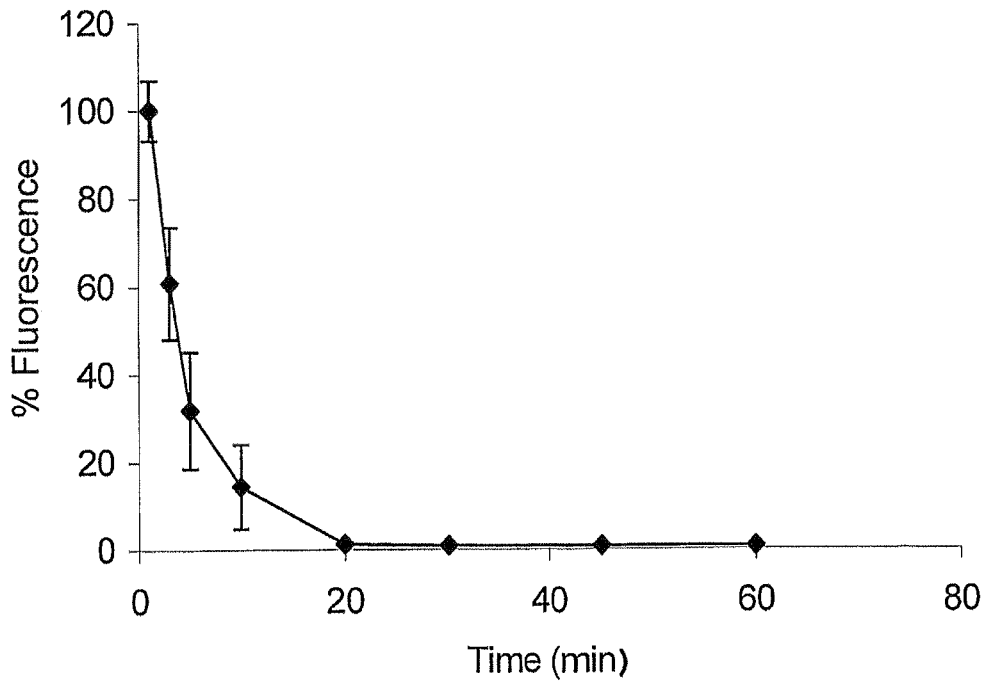
FIG. 2 shows the trend of pre-corneal permanence time of a solution containing arabinogalactan according to the invention, evaluated by determining a fluorescent derivative of arabinogalactan.

The attached FIG. 2 shows the percentage decrease in fluorescence of FITC-AG in the tear fluid over time, taking as 100% the fluorescence of product after 1 minute. Fluorescence is always high 10 minutes after administration, decreases after 20 minutes, and is still appreciable after 60 minutes, highlighting the prolonged permanence of AG in the pre-corneal region.

2. Induction and Treatment of Dry Eye Syndrome

The present study used an arabinogalactan solution (FiberAid® AG, Larex®) in water, hereinafter referred to as AG-Sol, with an AG concentration of 5% w/w, rendered isotonic by adding a suitable quantity of mannitol (4.41% w/w) and having a pH of 6.46.

For preparing the AG-Sol composition, a quantity of accurately weighed polymer was dispersed in deionised water (Milli-Q, Millipore) and the solution thus obtained was heated at 80° C. for 30 minutes under stirring with a magnetic stirrer. After cooling, the mannitol was added.

The solution thus obtained was filtered under a laminar flow hood by means of 0.22 μm sterile filters (Minisart Sartorius) and packaged in glass vials.

To assess the influence of arabinogalactan on lachrymation, in cases where the corneal epithelial lesions are associated with dry eye syndrome, an in vivo experiment was carried out.

The tests were carried out by using New Zealand albino rabbits weighing 2-2.5 kg.

One drop of an aqueous solution of 1.0% atropine sulphate (AS), 3 times a day (at 9 am, 1 pm and 5 pm) for 5 consecutive days, was instilled in both eyes of the animals in order to decrease lachrymal production and induce dry eye (S. Burgalassi et al., 1999, *Ophthalm. Res.*, 31, 229-235). After 5 minutes of each AS administration, 50 μl of the AG-Sol composition containing arabinogalactan was instilled in only their right eye.

The animals underwent the Schirmer I test at time 0 (prior to treatment) and on the $2^{nd}$, $3^{rd}$, $4^{th}$ and $5^{th}$ day after the start of treatment. The test envisages the measurement, once a day, of the quantity of tear fluid secreted. The determination was carried out before each administration of the solutions (AS and AG-Sol) by means of bibula paper strips (Alfa Intes) placed in the lower conjunctival fornix of each eye of the rabbit. The rise of the tear fluid along the bibula paper strips was measured in mm. The values obtained for the eyes treated with only atropine sulphate were compared with those obtained for the eyes treated with the arabinogalactan solution according to the invention.

The base value of lachrymal secretion was measured in a group of control animals on which no pharmacological treatment was carried out.

Figure 3:
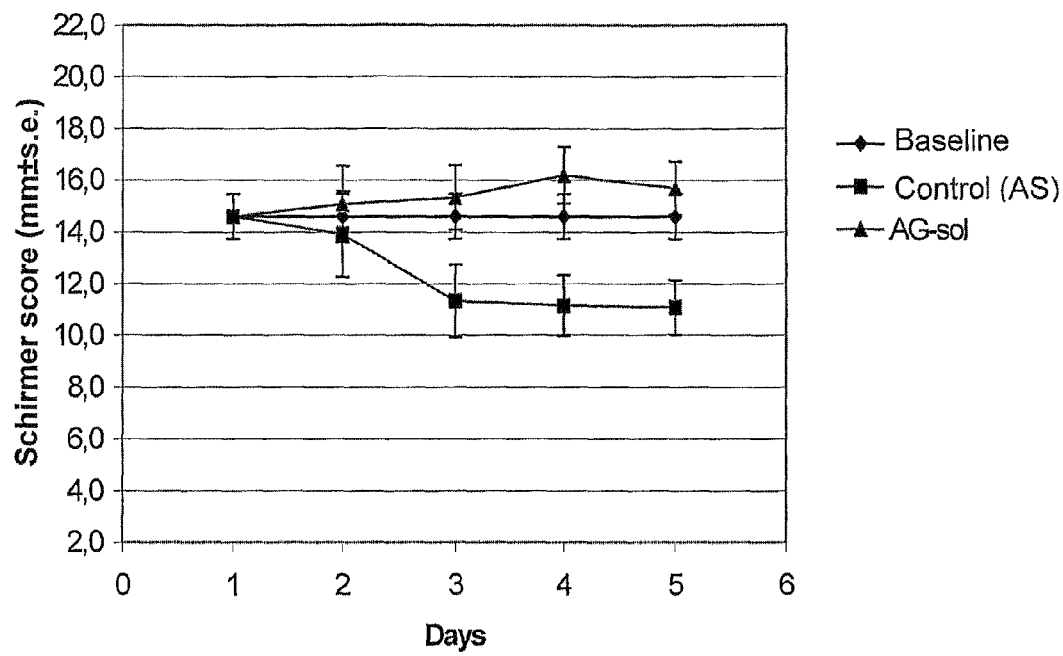
FIG. 3 shows the results obtained with the Schirmer I test carried out on rabbits treated with atropine sulphate (AS) in order to experimentally induce dry eye; in one eye of said rabbits a composition containing arabinogalactan according to the invention (AG-Sol) was also administered, as treatment.

The results obtained are reported graphically in FIG. 3 of the attached drawings. The figure shows how the AG-Sol solution has a protective effect against the onset of dry eye.

Moreover, on days 3, 4 and 5 after the start of treatment, the degree of alteration of the corneal epithelium caused by dry eye was assessed by observation with a slit lamp equipped with a blue filter, after colouring the cornea with 10 µl of an aqueous solution at 1% w/w of fluorescein. In the case of epithelial alterations, areas of colour on the corneal surface are observed: fluopositive eye.

Table 4 below reports the results obtained, as a percentage of fluopositive eyes out of the total of treated eyes. The same results are reported in the histogram of FIG. 4 attached, which graphically compares the percentage of eyes resulting fluopositive after treatment with the AG-Sol solution with respect to the percentage of fluopositive eyes in the control animals only treated with AS.

TABLE 4

Results obtained through observation by slit lamp

| No. | 3$^{rd}$ day DX (treated) | SX | 4$^{th}$ day DX (treated) | SX | 5$^{th}$ day DX (treated) | SX |
|---|---|---|---|---|---|---|
| 1 | − | + | − | − | − | − |
| 2 | − | − | − | − | − | + |
| 3 | − | − | − | + | − | − |
| 4 | − | + | − | + | + | + |
| 5 | − | − | − | + | − | − |
| 6 | − | + | − | + | − | − |
| 7 | − | − | − | + | − | + |
| 8 | + | − | − | − | + | + |
| 9 | − | − | + | + | − | + |
| 10 | − | − | − | − | − | + |
| 11 | − | + | − | − | − | + |
| 12 | − | − | + | − | − | − |
| sum | 1 | 4 | 2 | 6 | 2 | 7 |
| fluopositivity % | 8.33 | 33.33 | 16.67 | 50.00 | 16.67 | 58.33 |

Figure 4:
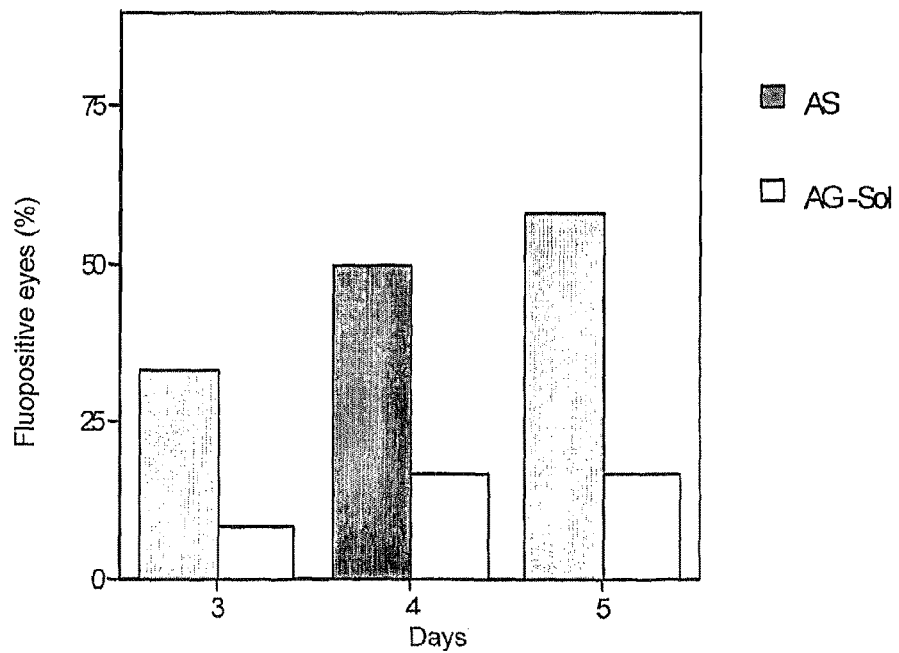
FIG. 4 shows a histogram of the results of a corneal epithelium alteration test carried out with fluorescein and observation by slit lamp carried out on the same rabbits of FIG. 3.

From the results shown in Table 4 and FIG. 4 it is possible to note how in the untreated eyes the percentage of fluopositivity increases day by day, and on 5$^{th}$ day of treatment reaches almost 60%, while in the eyes treated with the AG-Sol solution, the percentage of fluopositivity remains constant between the 4$^{th}$ and 5$^{th}$ day of treatment, at a much lower value of about 17%.

3. Evaluation of the Re-Epithelisation Capacity

The test reported below assesses the recovery time of a lesion produced on rabbit cornea after administration of the following compositions:

1. AG-Sol aqueous solution (5% AG, 4.41% mannitol;
2. TS-polysaccharide (TSP) 0.04% aqueous solution;
3. Hyaluronic acid (HA) 0.00144% aqueous solution.

It must be noted that, since the aim of the products according to the invention is that of providing lachrymal supplements which are not as viscous as artificial tears of the prior art based on polysaccharides so that they be particularly useful for contact lens users, the concentration of reference solutions 2) and 3) containing TSP and HA was chosen so as to have solutions with the same rheological behaviour (i.e. Newtonian) and the same viscosity value as the AG-Sol solution.

The test was conducted on New Zealand albino rabbits weighing 2-2.5 kg. The rabbits were anaesthetised by intramuscular injection (0.15 ml/kg) of Zoletil 100® (Laboratories Virdac, France) and the eye was kept open by using a blefarostat and anaesthetised on the surface by instilling 10 µl of oxybuprocaine hydrochloride (Novesina®, MiPharm, Italy).

In order to cause the corneal lesion, a microbiology paper disc of 6 mm diameter imbued with 10 µl of n-heptanol was placed on the central region of the cornea for 60 seconds. After removing the disc, the ocular surface was thoroughly washed with 1 ml of physiological solution (Burgalassi et al., 2000, *Eur. J. Opthalmol.*, 10, 71-76).

At time 0 (immediately after removal of the imbued paper and washing) and 3, 7, 18, 24, 27, 29, 31, 34, 41, 44, 48 and 51 hours after producing the lesion, the ocular surface was coloured with 10 µl of an aqueous solution of sodium fluorescein at 1% w/w and the diameter of the lesion was measured by means of a specific micrometer.

The treated animals received 100 µl of the examined solutions in the damaged eye 5 times a day (at 9 am, 11 am, 1 pm, 3 pm and 5 pm).

One group of animals, on which the corneal lesion had been carried out, was left to heal spontaneously and was used as a control group.

FIG. 5 of the attached drawings graphically reports the recovery trend of the corneal lesion of the animal groups over time. The data have been reported as a percentage decrease of the area of the lesion, taking as 100% the area at time 0. The same data are reported numerically in Table 5 below.

TABLE 5

Corneal lesion recovery test

| Time (hours) | Control (area %) | S.E. | AG-Sol (area %) | S.E. | TSP (area %) | S.E. | HA (area %) | S.E. |
|---|---|---|---|---|---|---|---|---|
| 0 | 100 | 0 | 100 | 0 | 100 | 0 | 100 | 0 |
| 3 | 100 | 0 | 100 | 0 | 100 | 0 | 100 | 0 |
| 7 | 87.1 | 9.14 | 72.358 | 2.918 | 79.167 | 3.076 | 91.071 | 4.593 |
| 18 | 55 | 4.1 | 44.44 | 0 | 61.033 | 5.075 | 59.293 | 7.591 |
| 24 | 31.62 | 4.35 | 29.236 | 3.065 | 31.859 | 2.117 | 41.863 | 3.64 |
| 27 | 26.91 | 1.57 | 18.839 | 1.833 | 23.627 | 1.637 | 30.95 | 2.183 |
| 29 | 25.205 | 4.545 | 15.838 | 1.211 | 15.508 | 2.273 | 20.121 | 3.362 |
| 31 | 16.29 | 4.38 | 7 | 1 | 13.657 | 2.688 | 14.384 | 2.101 |
| 34 | 11.72 | 4.28 | 3.812 | 1.047 | 7.098 | 1.782 | 7.213 | 1.249 |
| 41 | 7.12 | 2.098 | 1.062 | 0.981 | 2.568 | 1.336 | 5.083 | 2.663 |
| 44 | 5.2 | 2.3 | 0.695 | 0.695 | 0.817 | 0.653 | 2.847 | 1.663 |
| 48 | 3.7 | 3.7 | 0.001 | 0 | 0.17 | 0.17 | 0.111 | 0.099 |
| 51 | 0 | 0 | 0 | 0 | 0 | 0 | 0 | 0 |

From the above table, as well as from FIG. 5, it is possible to note that starting from 27 hours after administration of the compositions, only the composition according to the present invention, AG-Sol, shows a significantly different recovery rate than the control value. In fact, while AG-Sol presents statistically significant differences 27, 29, 31, 34 and 41 hours after the start of the treatment, for the other compositions this difference is significant only with TSP after 29 hours.

4. Evaluation of the Re-Epithelising Capacity in the Presence of Benzalkonium Chloride The test assesses the recovery time of a lesion produced on the rabbit cornea after administration of the following compositions:

1) AG-Sol aqueous solution (5% AG, 4.41% mannitol).
2) AG-Bz aqueous solution (5% AG, 4.00% mannitol, 0.01% benzalkonium chloride).

The test was carried out on New Zealand albino rabbits weighing 2-2.5 kg. The rabbits were anaesthetised by intramuscular injection (0.15 ml/kg) of Zoletil 100® (Laboratories Virdac, France), and the eye was kept open by using a blefarostate and anaesthetised on the surface by instilling 10 µl of oxybuprocaine hydrochloride (Novesina®, MiPharm, Italy).

In order to cause the corneal lesion, a microbiology paper disc of 6 mm diameter imbued with 10 µl of n-heptanol was placed on the central region of the cornea for 60 seconds. After removing the disc, the ocular surface was thoroughly washed with 1 ml of physiological solution (Burgalassi et al., 2000, *Eur. J. Opthalmol.*, 10, 71-76).

At time 0 (immediately after removal of the imbued paper and washing) and 3, 7, 18, 24, 27, 29, 31, 34, 41, 44, 48 and 51 hours after producing the lesion, the ocular surface was coloured with 10 µl of an aqueous solution of sodium fluorescein at 1% w/w and the diameter of the lesion was measured by means of a specific micrometer.

The treated animals received 100 µl of the examined solutions in the damaged eye 5 times a day (at 9 am, 11 am, 1 pm, 3 pm and 5 pm).

One group of animals, on which the corneal lesion had been carried out, was left to heal spontaneously and was used as a control group.

FIGS. 6 and 6a graphically show the corneal lesion recovery trend, at two different levels of detail, for the animal groups over time. The data have been reported as a percentage decrease of the area of the lesion, taking as 100% the area at time 0.

It is possible to note that the presence of benzalkonium chloride modifies the recovery rate of AG by slowing it down: complete recovery in the animals treated with the AG-Bz composition occurs after 51 hours, while in the animals treated with AG-Sol it occurs as early as 44 hours after. That is why using both products in a composition aimed at protecting the cornea is disadvantageous.

Histological Evaluation of Treated Corneas

To assess whether the re-epithelisation process—besides providing for the complete healing of the experimentally induced lesions—also produced the proper stratification of epithelial cells, so as to reconstitute the native corneal structure, a histological analysis was carried out.

Samples of corneas collected 24 hours after producing the corneal lesion, after complete recovery (when no further fluorescein detection was observed on the epithelium) and 1 week after recovery, were fixed in a 10% paraformaldehyde solution in a 0.1 M pH 7.4 phosphate buffer. The samples were then subjected to several washings with a buffer for 12 hours, dehydrated in a series of ethyl alcohol solutions of increasing concentration and embedded at 4° C. in a specific resin for optical microscopy (JB-4, Embedding kit, Polysciences Inc.). The embedded sample was sectioned by microtomy and subjected to Nissl colouring before being observed under a microscope.

24 hours after producing the lesion, the physiological reparative mechanism was evident, since there was a shift and migration of the adjacent integral epithelial cells to the damaged area, with the formation of a monolayer. The epithelium, instead, re-established a natural thickness (55-60 µm in the central region of the cornea) and stratified structure only when complete recovery occurred, when the interruption of the physiological mechanism of cell surface scaling had ceased and complete coverage of the minus region and regeneration of the epithelial elements assured the restoration of normal structural characteristics. The conditions remained unchanged a week after recovery, indicating that the regeneration process was complete.

The treatments carried out after producing the corneal lesion, performed with the same products reported in the preceding section 3 of the biological tests, led to a decrease of lesion recovery time to different degrees, depending on the product used. This led to the assumption of a different influence of the used polymers on the repair mechanism. It thus became necessary to investigate the re-epithelisation phases in order to highlight any differences in the morphological aspect of the tissue.

To this end, the re-epithelisation capacity evaluation method (section 3, biological tests) was repeated by performing the lesion and treatments with the polymeric compositions as reported above. The animals were immediately sacrificed before complete recovery of the corneal lesion, that is, when the latter was no longer measurable with the equipment used, but fluorescein captation on the ocular surface was still visible.

The corneal samples thus treated were subjected to histological analysis with the same procedure as indicated above, and the thickness of the reconstituted epithelium was measured in each case.

Measurement was performed at the same distance each time from the re-growth margin, and highlighted differences in thickness of the epitheliums reformed after the various treatments. In fact, the following results were obtained:

Untreated control (spontaneous recovery), 6 µm;
sample treated with AG-Sol (5% AG, 4.41% mannitol), 18 µm;
sample treated with 0.5% TS-polysaccharide, 18 µm;
sample treated with 0.2% hyaluronic acid, 12 µm.

These results show that the epithelium going to reconstitute the deficient area does not yet have a physiological thickness in any of the cases observed, even if in the samples treated with the AG-Sol and TS-polysaccharide compositions the thickness is considerably greater than that of the control left to recover spontaneously.

Observation of the respective images (not shown) also highlighted the morphological diversity between the corneal samples under examination. There are, in fact, considerable differences in the arrangement of the neo-epithelium in the four cases examined:

The sample deriving from the control eye showed a still not well-organised structure, with little or not stratification.
The epithelium treated with the AG-Sol composition showed a close similarity to the native epithelium, as regards tissue arrangement.
The sample treated with TS-polysaccharide showed a poorly stratified neo-tissue, despite the fact that the thickness of this epithelium was the same as the one of the sample treated with AG-Sol; in fact, it was often a matter of a few cells of large size, much larger than the norm.

Finally, treatment with HA produced a discrete stratification of the neo-epithelium, even if the final thickness obtained was lower.

These results lead to the conclusion that the greater recovery rate of a corneal lesion determined after treatment with AG-containing composition is due to the stimulation of the regeneration of the epithelial elements that this product causes. The greater replication capacity of the epithelial cells leads to an early stratification of the tissue, which thus manages to have a greater number of cells to cover the deficit zone.

Cell Toxicity Studies

The cytotoxicity of solutions containing AG alone or in the presence of benzalkonium chloride (Bz) was evaluated. Mother solutions of the polymer were prepared (1. AG 5% w/w; 2. AG 5% w/w+Bz 0.01% w/w) directly in Dulbecco's modified Eagles medium (DMEM, Sigma Chemical Co., St. Louis, Mo., USA). These solutions were then diluted 1:2, 1:5, 1:10, 1:100 and 1:1000 still by using DMEM.

The cell line used consisted of rabbit corneal epithelial cells (RCE SV40 transformed, N. 95081046, ECACC, G.B.). The RCE line was created by infecting primary cultures of rabbit corneal epithelial cells with a recombinant retrovirus SV-40. The cells show the typical paved morphology of epitheliums and a stratification capacity, as well as the development of desmosomes and microvilli.

The cell growth medium was Dulbecco's modified Eagles medium (DMEM, Sigma Chemical Co., St. Louis, Mo., USA) enriched with Ham's nutrient mixture F12 (1:1), L-glutamine (1% v/v, 2 mM), penicillin (100 Ul/ml), streptomycin (0.1 mg/ml), amphotericin B (0.25 µg/ml), heat deactivated bovine foetal serum (15% v/v) (Gibco, Great Britain), insulin (5 µg/ml), epidermal growth factor (10 ng/ml) (Sigma Chemical Co., St. Louis, Mo., USA). The cells grew at 37° C. in a humidity saturated atmosphere with 5% $CO_2$.

Evaluation of the degree of toxicity of the solutions tested on the RCE cells was carried out by means of the colorimetric method, using the commercially available cell proliferation reagent WST-1 (Roche Diagnostics® S.p.A., Monza). The test is based on the splitting, through mitochondrial activity, of the tetrazolium salt WST-1 to a soluble coloured compound (formazan). Since the transformation can only be made by living cells, the quantity of formazan produced is directly correlated to the number of living cells.

The RCE cells were placed on 96-well slides (Corning Costar® Italia, Milan) at a concentration of $5 \times 10^3$ cells/well. After 24 hours, at 90% confluence, the growth medium was removed and replaced with the solution to be tested (100 µl of solution). After 60 minutes of contact (at 37° C., in a humidified atmosphere and with 5% $CO_2$), the reaction medium was removed and the cells were washed twice with DMEM F12; 100 µl of fresh growth medium and 10 µl of WST-1 reagent were then added in each well. The cells were again incubated for 2 hours (at 37° C., in a humidified atmosphere and with 5% $CO_2$) and the slides were gently shaken for 9 seconds; the absorbance of the medium was measured at 450 nm by using an appropriate spectrophotometer (Microtiter reader 550®, Bio-Rad Laboratories, Hercules, Calif.). The optimal incubation time with the WST-1 reagent had been determined through a series of preliminary experiments.

The spectrophotometric reading was performed against a "blank" well containing a mixture of only medium and WST-1 (100 and 10 µl, respectively), without cells. The results were expressed as the percentage absorbance of the treated wells ($Abs_{tr}$) with respect to the untreated wells (control, $Abs_c$), containing cells treated with only the medium with no pharmaceutical product, according to the following formula:

$$\% \text{ living cells} = \frac{Abs_{tr} \times 100}{Abs_c}$$

The results are shown graphically in FIG. 7, in which cell vitality is expressed as a percentage with respect to the AG concentration logarithm, when the cells were treated with solutions containing only AG or the AG+Bz mixture. AG did not show any cytotoxicity at all the tested concentrations. The addition of Bz caused an increase in toxicity, above all, in the higher concentrations. The presence of benzalkonium chloride thus involves a significant cytotoxicity and, in addition, as demonstrated by the in-vivo experiments, also a decrease in the re-epithelisation activity of AG.

The present invention has been disclosed with reference to some specific embodiments thereof, but it is to be understood that variations or modifications can be brought by persons skilled in the art without departing from the scope of the appended claims.

The invention claimed is:

1. An ophthalmic composition for use as a tear fluid substitute to enhance recovery of corneal and conjunctive lesions and inflammation, said ophthalmic composition comprising from 1% to 10% by weight of arabinogalactan in an aqueous solution, wherein
    the arabinogalactan is larch arabinogalactan and the composition does not contain benzalkonium chloride.

2. An ophthalmic composition according to claim 1, containing from 3% to 5% by weight of arabinogalactan in an aqueous solution.

3. An ophthalmic composition according to claim 1, also containing one or more tonicity-adjusting agents.

4. An ophthalmic composition according to claim 3, wherein the said one or more tonicity-adjusting agents are present in the aqueous solution in such a quantity as to provide a solution with osmolarity between 150 and 300 mOsm/L.

5. An ophthalmic composition according to claim 4, wherein the said one or more, tonicity-adjusting agents are chosen from the group consisting of: mannitol, sodium chloride, potassium chloride, dextrose, boric acid and sorbitol.

6. An ophthalmic composition according to claim 1, also containing one or more pharmaceutically acceptable acids or bases, as pH correctors.

7. An ophthalmic composition according to claim 1, also containing one or more buffers.

8. An ophthalmic composition according to claim 7, wherein the said buffers are chosen from the group consisting of: phosphate buffer, borate buffer, citrate buffer, bicarbonate buffer, trizma buffer tri-hydroxymethylaminomethane).

9. An ophthalmic composition according to claim 1, also containing one or more preservatives, except for benzalkonium chloride.

10. An ophthalmic composition according to claim 9, wherein the said preservatives are chosen from the group consisting of: sodium merthiolate or thimerosal, phenylmercuric nitrate or acetate, phenylethyl alcohol, methyl-, ethyl- and propylparaben, chlorohexidine acetate or gluconate and chlorobutanol.

11. An ophthalmic composition according to claim 1, also containing one or more chelating agents.

12. An ophthalmic composition according to claim 11, wherein the said chelating agent is EDTA.

13. A method of treating corneal or conjunctival lesions and inflammation, the method comprising administering to a subject having corneal or conjunctival lesions and inflammation, an ophthalmic composition according to claim 1.

14. The method according to claim 13, wherein the said ophthalmic composition comprises from 3% to 5% by weight of arabinogalactan.

15. The method according to claim 13, wherein the said ophthalmic composition is in the form of a tear fluid substitute indicated for contact lens users.

16. The method according to claim 13, wherein the said ophthalmic composition is in the form of a tear fluid substitute for the treatment of keratoconjunctival lesions and inflammations.

17. The method according to claim 13, wherein the corneal lesions and inflammation are caused by contact lens use.

18. The method according to claim 13, wherein the ophthalmic composition comprises one or more tonicity-adjusting agents.

19. The method according to claim 18, wherein the said one or more tonicity-adjusting agents are present in the aqueous solution in such a quantity as to provide a solution with osmolarity between 150 and 300 mOsm/L.

20. The method according to claim 19, wherein the said one or more tonicity-adjusting agents are chosen from the group consisting of:
mannitol, sodium chloride, potassium chloride, dextrose, boric acid and sorbitol.

21. The method according to claim 13, wherein the ophthalmic solution comprises one or more pharmaceutically acceptable acids or bases, as pH correctors.

22. The method according to claim 13, wherein the ophthalmic composition comprises one or more buffers.

23. The method according to claim 22, wherein the said buffers are chosen from the group consisting of: phosphate buffer, borate buffer, citrate buffer, bicarbonate buffer, trizma buffer tri-hydroxymethylaminomethane).

24. The method according to claim 13, wherein the ophthalmic composition comprises one or more preservatives, except for benzalkonium chloride.

25. The method according to claim 24, wherein the said preservatives are chosen from the group consisting of: sodium merthiolate or thimerosal, phenylmercuric nitrate or acetate, phenylethyl alcohol, methyl-, ethyl- and propylparaben, chlorohexidine acetate or gluconate and chlorobutanol.

26. The method according to claim 13, wherein the ophthalmic composition comprises one or more chelating agents.

27. The method according to claim 26, wherein the said chelating agent is EDTA.

* * * * *